(12) United States Patent
Jenkins et al.

(10) Patent No.: US 11,167,109 B2
(45) Date of Patent: **\*Nov. 9, 2021**

(54) DEVICES AND METHOD FOR MAXILLARY SINUS LAVAGE

(71) Applicant: Acclarent, Inc., Irvine, CA (US)

(72) Inventors: Thomas R. Jenkins, Alameda, CA (US); Jessica Liberatore, San Mateo, CA (US); Sandra W. Ruggles, Sunnyvale, CA (US); Jessica K. Chan, Sunnyvale, CA (US)

(73) Assignee: Acclarent, Inc., Irvine, CA (US)

( * ) Notice: Subject to any disclaimer, the term of this patent is extended or adjusted under 35 U.S.C. 154(b) by 455 days.

This patent is subject to a terminal disclaimer.

(21) Appl. No.: 16/190,227

(22) Filed: Nov. 14, 2018

(65) Prior Publication Data

US 2019/0143080 A1 May 16, 2019

Related U.S. Application Data

(63) Continuation of application No. 15/787,632, filed on Oct. 18, 2017, now Pat. No. 10,166,369, which is a (Continued)

(51) Int. Cl.
*A61M 25/01* (2006.01)
*A61M 25/00* (2006.01)
(Continued)

(52) U.S. Cl.
CPC .......... *A61M 25/0147* (2013.01); *A61B 1/07* (2013.01); *A61M 3/0279* (2013.01);
(Continued)

(58) Field of Classification Search
CPC .......... A61M 25/0068; A61M 25/0152; A61M 25/0041; A61M 25/0067; A61M 25/007;
(Continued)

(56) References Cited

U.S. PATENT DOCUMENTS 3,885,561 A * 5/1975 Cami ................ A61M 25/0108
604/247
5,152,749 A 10/1992 Giesy et al.
(Continued)

OTHER PUBLICATIONS

International Search Report and Written Opinion dated Aug. 1, 2013 for Application No. PCT/US2013/036372, 12 pgs.
(Continued)

*Primary Examiner* — Nathan R Price
*Assistant Examiner* — Anh Bui
(74) *Attorney, Agent, or Firm* — Frost Brown Todd LLC

(57) ABSTRACT

A lavage catheter for the treatment of a maxillary sinus is described. The catheter comprises a proximal portion and a distal portion. The distal portion comprises an irrigation tip. The irrigation tip has a tip opening through which fluid may be delivered by one handed operation of the catheter. A method for lavaging the maxillary sinus includes inserting the lavage catheter into a patient's anatomy and advancing the irrigation tip into the maxillary sinus using one hand.

20 Claims, 8 Drawing Sheets

Related U.S. Application Data continuation of application No. 13/800,163, filed on Mar. 13, 2013, now abandoned.

(60) Provisional application No. 61/675,595, filed on Jul. 25, 2012, provisional application No. 61/623,730, filed on Apr. 13, 2012.

(51) Int. Cl.
*A61B 1/07* (2006.01)
*A61M 3/02* (2006.01)
*A61B 1/233* (2006.01)

(52) U.S. Cl.
CPC ...... *A61M 25/007* (2013.01); *A61M 25/0068* (2013.01); *A61M 25/01* (2013.01); *A61M 25/0152* (2013.01); *A61B 1/233* (2013.01); *A61M 25/0041* (2013.01); *A61M 25/0113* (2013.01); *A61M 2025/0004* (2013.01); *A61M 2025/0006* (2013.01); *A61M 2025/0175* (2013.01); *A61M 2210/0681* (2013.01)

(58) Field of Classification Search
CPC .. A61M 2025/0004; A61M 2025/0006; A61M 2025/017; A61M 2025/0041
See application file for complete search history.

(56) References Cited

U.S. PATENT DOCUMENTS

| | | |
|---|---|---|
| 7,645,272 B2 | 1/2010 | Chang et al. |
| 7,654,997 B2 | 2/2010 | Makower et al. |
| 7,803,150 B2 | 9/2010 | Chang et al. |
| 8,241,266 B2 | 8/2012 | Keith et al. |
| 8,414,473 B2 | 4/2013 | Jenkins et al. |
| 8,764,726 B2 | 7/2014 | Chang et al. |
| 8,979,888 B2 | 3/2015 | Morriss et al. |
| 9,579,448 B2 | 2/2017 | Chow et al. |
| 9,814,379 B2 | 11/2017 | Makower et al. |
| 10,166,369 B2 * | 1/2019 | Jenkins ............. A61M 25/0068 |
| 2006/0095006 A1 | 5/2006 | Chang et al. |
| 2007/0185435 A1 | 8/2007 | Sampson |
| 2008/0097391 A1 | 4/2008 | Feinberg et al. |
| 2008/0183128 A1 * | 7/2008 | Morriss ............. A61M 25/0068 604/35 |
| 2008/0249500 A1 | 10/2008 | Keith et al. |
| 2009/0024084 A1 | 1/2009 | Khosla et al. |
| 2012/0101433 A1 | 4/2012 | Alvarez |
| 2013/0165873 A1 | 6/2013 | Morriss et al. |
| 2013/0184574 A1 | 7/2013 | Newhauser et al. |
| 2013/0274600 A1 | 10/2013 | Jenkins et al. |
| 2015/0328394 A1 | 11/2015 | Chow et al. |
| 2018/0104404 A1 | 4/2018 | Ngo-Chu |

OTHER PUBLICATIONS

Mexican Office Action dated Dec. 30, 2016 for Application No. MX/a/2014/012379, 4 pages.
U.S. Appl. No. 61/623,730, filed Apr. 13, 2012.
U.S. Appl. No. 61/675,595, filed Jul. 25, 2012.

* cited by examiner

DEVICES AND METHOD FOR MAXILLARY SINUS LAVAGE

CROSS-REFERENCES TO RELATED APPLICATIONS

This patent application is a continuation of U.S. patent application Ser. No. 15/787,632 filed on Oct. 18, 2017 and issued as U.S. Pat. No. 10,166,369 on Jan. 1, 2019, which is a continuation of U.S. patent application Ser. No. 13/800,163 filed on Mar. 13, 2013 and published as US 2013-0274600 A1 on Oct. 17, 2013, now abandoned, which claims priority to U.S. Patent Application No. 61/675,595 filed on Jul. 25, 2012 and also claims priority to U.S. Patent Application No. 61/623,730 filed on Apr. 13, 2012, the entire disclosures of which are expressly incorporated herein by reference.

FIELD OF THE INVENTION

The present invention relates, in general, to medical devices and, in particular, to medical devices and related methods for the treatment of sinus conditions.

BACKGROUND OF THE INVENTION

The paranasal sinuses are hollow cavities in the skull connected by small openings, known as ostia, to the nasal canal. Each ostium between a paranasal sinus and the nasal cavity is formed by a bone covered by a layer of mucosal tissue. Normally, air passes into and out of the paranasal sinuses through the ostia. Also, mucus is continually formed by the mucosal lining of the sinuses and drains through the ostia and into the nasal canal.

Sinusitis is a general term that refers to inflammation in one or more of the paranasal sinuses. Acute sinusitis can be associated with upper respiratory infections or allergic conditions, which may cause tissue swelling and temporarily impede normal trans-ostial drainage and ventilation of the sinuses, thereby resulting in some collection of mucus and possibly infection within the sinus cavities. Chronic sinusitis is a long term condition characterized by persistent narrowing or blockage of one or more sinus ostia, resulting in chronic infection and inflammation of the sinuses. Chronic sinusitis is often associated with longstanding respiratory allergies, nasal polyps, hypertrophic nasal turbinates and/or deviated internasal septum. While acute sinusitis is typically caused by infection with a single pathogen (e.g., one type of bacteria, one type of virus, one type of fungus, etc.), chronic sinusitis is often associated with multiple pathogen infections (e.g., more than one type of bacteria or more than one genus of micro-organism).

Chronic sinusitis, if left untreated, can result in irreparable damage to the tissues and/or bony structures of the paranasal anatomy. The initial treatment of chronic sinusitis usually involves the use of drugs such as decongestants, steroid nasal sprays and antibiotics (if the infection is bacterial). In cases where drug treatment alone fails to provide permanent relief, surgical intervention may be indicated.

The most common surgical procedure for treating chronic sinusitis is functional endoscopic sinus surgery (FESS). FESS is commonly performed using an endoscope and various rigid instruments inserted through the patient's nostril. The endoscope is used to visualize the positioning and use of various rigid instruments used for removing tissue from the nasal cavity and sinus ostia in an attempt to improve sinus drainage.

A technique known as the Balloon Sinuplasty™ procedure and a system for performing the procedure has been developed by Acclarent Inc, of Menlo Park, Calif. for treatment of sinusitis. A number of US patents and patent applications including U.S. Pat. Nos. 7,645,272, 7,654,997, and 7,803,150 describe various embodiments of the Balloon Sinuplasty™ procedure as well as various devices useable in the performance of such procedure. In the Balloon Sinuplasty™ procedure, a guide catheter is inserted into the nose and positioned within or adjacent to the ostium of the affected paranasal sinus. A guidewire is then advanced through the guide catheter and into the affected paranasal sinus. Thereafter, a dilation catheter having an expandable dilator (e.g. an inflatable balloon) is advanced over the guidewire to a position where the dilator is positioned within the ostium of the affected paranasal sinus. The dilator is then expanded, causing dilation of the ostium and remodelling of bone adjacent to the ostium, without required incision of the mucosa or removal of any bone. The catheters and guidewire are then removed and the dilated ostium allows for improved drainage from and ventilation of the affected paranasal sinus.

Before or after performing a FESS or Balloon Sinuplasty™ procedure, it may be useful or necessary to irrigate the paranasal sinus. A device described in US 2008/0183128, may be used for irrigating a paranasal sinus. The irrigation catheter may be advanced through a guide catheter and into an ostium or the sinus for purposes of, for example irrigation, suctioning, substance delivery and culture retrieval.

There is a continuing need for improved methods and devices for treating the paranasal sinus. Although the irrigation catheter described above is easy to use, it would be useful to provide an improved catheter for irrigating the maxillary sinuses.

SUMMARY OF THE INVENTION

In a first aspect, the invention is a catheter for the lavage of a maxillary sinus comprising a distal portion having an elongate shaft with a bend angle of between about 90 degrees and 140 degrees. The lavage catheter distal portion further has a distal irrigation tube that is in coaxial arrangement with the elongate shaft. An actuator that is located between a distal hub and a proximal hub is used for advancing the distal irrigation tube into the maxillary sinus. The lavage catheter further includes a proximal portion with an irrigation luer and irrigation tubing.

In one embodiment of the lavage catheter, the irrigation tip has a distal tip opening.

In another embodiment, the irrigation tip has and one or more radially facing openings.

In another embodiment the distal irrigation tube is a flexible material selected from the group consisting of nylon, polyethylene, polyether ether ketone or polyether block amides.

In a further embodiment, the distal irrigation tube is a polyether block amide.

In still another embodiment, the lavage catheter includes one or more direct visualization markers.

In another embodiment, the lavage catheter includes one or more radiographic markers.

In a further embodiment, the distal irrigation tube surrounds the elongate shaft.

In yet a further embodiment, the distal irrigation tube is surrounded by the elongate shaft.

In still another embodiment, the lavage catheter comprises an illuminating fiber.

In another embodiment, the distal irrigation tip has a tapered configuration.

In another aspect, the invention is a catheter for the lavage of a maxillary sinus. The catheter includes a distal portion and a proximal portion. The distal portion in includes an elongate shaft with a bend angle of between about 90 degrees and 140 degrees, a distal irrigation tube in coaxial arrangement with the elongate shaft, and a handle with an actuator. The proximal portion of the catheter has an irrigation luer and irrigation tubing. The actuator is useful for advancing the distal irrigation tube into the maxillary sinus.

In one embodiment, the actuator has a light access port and the distal portion of the catheter includes an illuminating fiber.

In another aspect, the invention is a kit for the lavage of a maxillary sinus. The kit includes a catheter and an endoscope. The catheter includes a distal portion and a proximal portion. The distal portion has an elongate shaft with a bend angle of between about 90 degrees and 140 degrees, a distal irrigation tube coaxially arranged with the elongate shaft, an illuminating fiber, and a handle with an actuator. The actuator has a light access port for insertion of the endoscope. The actuator is useful for advancing the distal irrigation tube into the maxillary sinus. The proximal portion of the catheter has an irrigation luer and irrigation tubing, In another aspect, the invention includes a method for lavaging a maxillary sinus. The method includes positioning a lavage catheter comprising a proximal portion, and a distal portion in the nasal anatomy. The distal portion comprises an irrigation tip. The method further includes connecting a fluid source to the irrigation catheter; with one hand, advancing the irrigation tip into the maxillary sinus; and delivering fluid to the maxillary sinus from the fluid source though the lavage catheter.

In a further embodiment, the method includes delivering the fluid at a flow rate of between 50 ml/min and 250 ml/min.

In yet another embodiment, the delivered fluid is selected from the group consisting of water, saline, contrast agents, antimicrobial agents anti-inflammatory agents, decongestants, mucous thinning agents, anesthetic agents, analgesic agents, anti-allergenic agents, allergens, anti-proliferative agents, hemostatic agents, cytotoxic agents, and biological agents or combinations of any of the above.

In another aspect, the invention is directed to a kit for the lavage of a maxillary sinus. The kit comprises a maxillary lavage catheter and a illuminating fiber connector. The catheter comprises a distal portion and a proximal portion. The catheter distal portion comprises an elongate shaft with a bend angle of between about 90 degrees and 140 degrees, a distal irrigation tube in coaxial arrangement with said elongate shaft, an illuminating fiber, and a handle. The handle comprises an actuator. The catheter proximal portion comprises an irrigation luer and irrigation tubing. The actuator is useful for advancing the distal irrigation tube into the maxillary sinus. The illuminating fiber connector connects the illuminating fiber to a light source, wherein the illuminating fiber connector allows for rotation of the catheter while the catheter is connected to the light source.

In another aspect, the invention is directed to a kit for the lavage of a maxillary sinus. The kit comprises a catheter and fluid delivery system. The catheter comprises a distal portion and a proximal portion. The distal portion comprises an elongate shaft with a bend angle of between about 90 degrees and 140 degrees, a distal irrigation tube in coaxial arrangement with the elongate shaft, an illuminating fiber, and a handle comprising an actuator. The proximal portion comprises an irrigation luer and irrigation tubing. The actuator is useful for advancing the distal irrigation tube into the maxillary sinus. The fluid delivery system provides for continuous fluid delivery to the catheter.

In a further embodiment, the fluid delivery system comprises a syringe, a fluid reservoir, a first one-way valve for directing fluid from the syringe into the catheter when pressure is applied to the syringe and a second one-way valve for directing fluid from the fluid reservoir into the catheter when pressure is released from the syringe.

DETAILED DESCRIPTION

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

Medical devices according to embodiments of the present invention are beneficial in that, for example, their configuration provides for a particularly efficient preparation and treatment of a patient's sinus and is mechanically simple. Moreover, the simplicity of the medical devices provides for them to be manufactured in a cost effective manner. In addition, the medical device according to embodiments of the present invention is sufficiently stiff that it can be beneficially employed to access sinus anatomy followed by a convenient suction and/or irrigation of the sinus.

Figure 1:
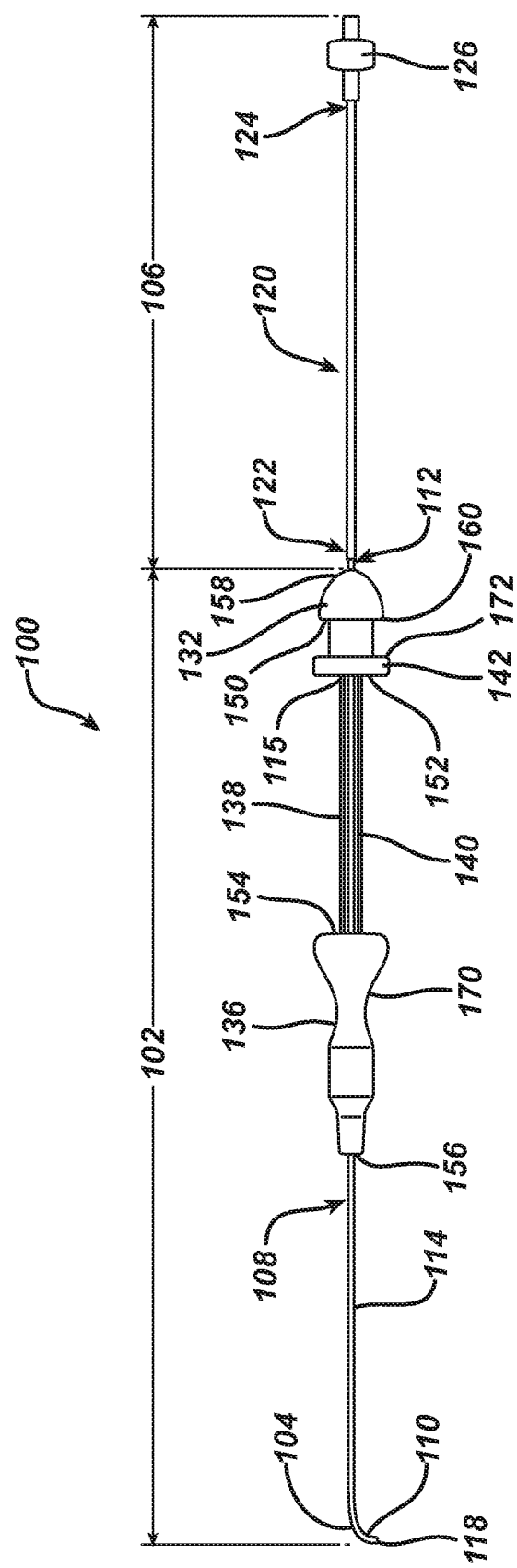
FIG. 1 is a side view of a medical device according to an embodiment of the present invention in a retracted configuration.

FIG. 1 is a side view of a maxillary lavage catheter 100 according to an embodiment of the present invention. The maxillary lavage catheter 100 has a distal portion 102 and a proximal portion 106.

The distal portion 102 in the embodiment shown in FIG. 1 includes an elongate shaft 108 with sufficient stiffness to access the maxillary sinus that further includes a distal end 110 and a proximal end 112. The distal end 110 of the elongate shaft 108 has a bend angle that is optimal for access to the maxillary sinus such that it can be maneuvered to access behind the uncinate process. Accordingly, the bend angle is between about 90° and 140°, often between about 100° and 130° and often about 110° or about 120°. The elongate shaft may be of any material that will maintain its shape when inserted into the patient's anatomy including but not limited to a polymeric material selected from the group including but not limited to nylon, polycarbonate, and styrene, or a biocompatible metal including but not limited to stainless steel, but will often be a stainless steel hypotube that may or may not be coated or colored, often in black, white or blue. Alternatively, the elongate shaft 108 may be made of a malleable material including but not limited to annealed stainless steel that can be shaped appropriately for accessing the maxillary sinus.

The distal portion 102 of the maxillary lavage catheter 100 additionally includes a distal irrigation tube 114 that is in coaxial arrangement elongate shaft 108. In the embodiment shown in FIG. 1, the distal irrigation tube 114 surrounds the elongate shaft 108, but in an alternative embodiment, the distal irrigation tube 114 may be surrounded by the elongate shaft 108. The distal irrigation tube 114 may be of any flexible material that can be used to extend into the maxillary sinus as will be described further below, including but not limited to a flexible, biocompatible polymer material, such as nylon, polyethylene, polyether ether ketone (PEEK), or polyether block amides (e.g. Pebax for example) and that may be braided or not braided. In the embodiment shown in FIG. 1, the material is Pebax.

The distal end 110 of the distal irrigation tube 114 includes a soft, atraumatic tip 118. The soft atraumatic tip 118 may be of a low durometer pebax material and it may be of tapered construction for easy access into the maxillary sinus. The atraumatic tip 118 may further have one or more radially facing openings to facilitate irrigation, often one, two or three openings of between about 0.5 to about 1.5 mm, often between about 0.8 and 1.0 mm. The lavage catheter 100 is designed to irrigate the sinus through the atraumatic tip 118 at a flow rate of between about 50 ml/min and 250 ml/min and often between about 75 ml/min and 125 ml/min. The diameter of the opening 212 of the atraumatic tip is between about 0.5 mm and 1.5 mm, and is often between about 0.9 mm and 1.0 mm. Further, instead of delivering fluid, a vacuum may be applied and a culture may be obtained by suctioning through the atraumatic tip 118.

The distal portion 102 of the maxillary lavage catheter 100 additionally includes a proximal hub 132 and a distal hub 136. Between the proximal hub 132 and the distal hub 136 are stiffening elements 138 and 140, and an actuator 142. The actuator 142 has a proximal end 150 and a distal end 152. The proximal end 112 of the elongate shaft 108 extends through the proximal hub 132 and connects to the distal end 122 of the proximal irrigation tube 120. The proximal end 115 of the distal irrigation tube 114 is connected to the distal end 152 of the actuator 142. The stiffening elements 138 and 140 extend from the proximal end of the distal hub 136 through the actuator 142 to the distal end 160 or proximal hub 132. As shown in FIG. 1, when the proximal irrigation tube 120 is fully retracted, the proximal end 150 of actuator 142 is adjacent to the distal end 160 of the proximal hub 132.

Figure 2:
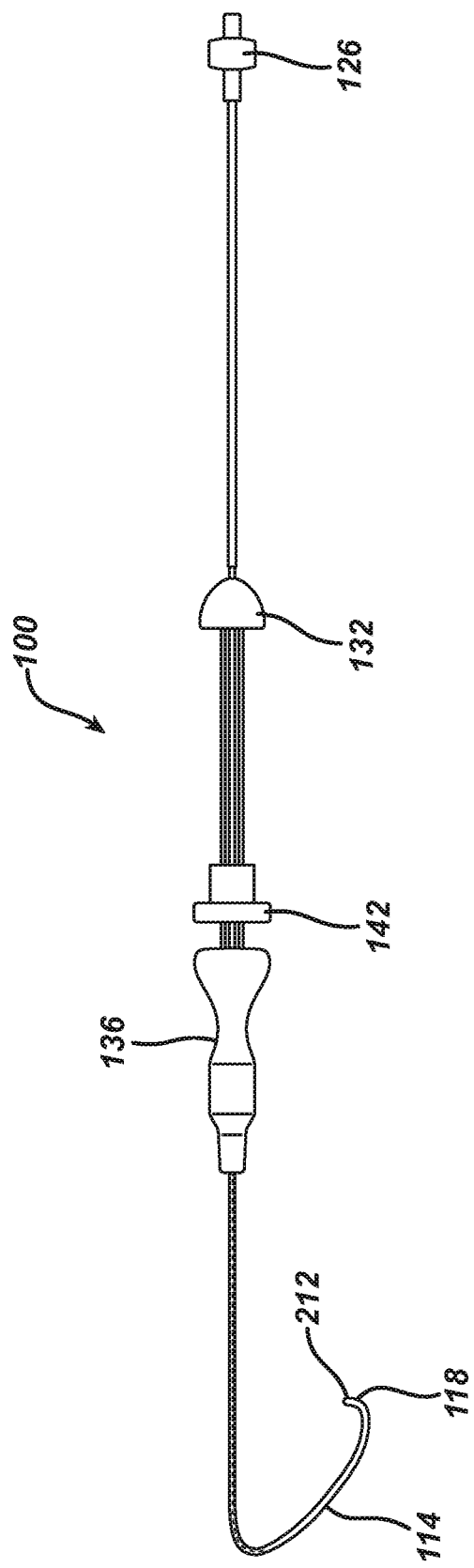
FIG. 2 is a side view of the medical device of FIG. 1 in an extended configuration.

The distal hub 136 and proximal hub 132 are configured for one-handed operation of the maxillary lavage catheter 100. The narrow portion 170 of the distal hub 136 may be for grasped while the ridge 172 on the actuator 142 is pushed toward the distal hub 136 with the thumb. Alternatively, the narrow portion 170 of the distal hub 136 is may be grasped by the thumb and one or more fingers while the ridge 172 on the actuator 142 can be drawn toward the distal hub 136 with one finger. In this way, as is shown in FIG. 2, the distal irrigation tube 114 is extended beyond the distal end 110 of the elongate shaft 108 and into the maxillary sinus. Similarly, removal from the nasal anatomy can be effected by the thumb or single finger of the physician user as pressure is applied on the ridge 172, pushing it away from the nasal anatomy, retracting the distal irrigation tube 114 and the removing the maxillary lavage catheter from the nasal anatomy. In an alternative embodiment, a spring may be included to automatically retract the distal irrigation tube 114 following irrigation of the maxillary sinus. Although the embodiments shown in FIGS. 1 and 2 shown the distal irrigation tube 114 coaxially surrounding the elongate shaft 108, contemplated herein is also a configuration where in the irrigation tube elongate shaft 108 coaxially surrounds the distal irrigation tube 114.

Figure 8:
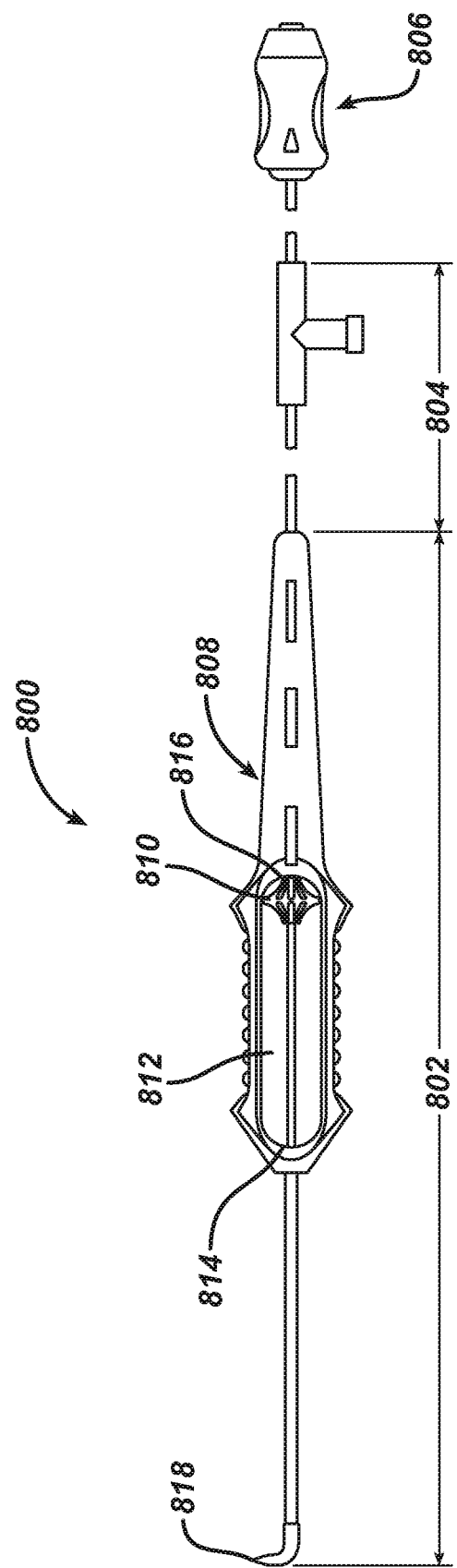
FIG. 8 is a top view of yet another embodiment of the medical device according to the invention.

Another embodiment of the maxillary lavage catheter 800 according to the invention is shown in FIG. 8 having a distal portion 802 and a proximal portion 804 and a light cable connector 806. In this embodiment, a handle 808 and an actuator 810 are included on the distal portion 802 of the catheter 800. The handle has an opening 812 with a distal end 814 and a proximal end 816. When the actuator 810 is seated against the proximal end 816 of the opening 812, the irrigation tubing (not shown, see FIG. 3) of the maxillary lavage catheter 800 is contained within the maxillary lavage catheter. When the actuator 810 is advanced in a one-handed fashion, with a single finger or thumb, and seated against the distal end 814 of the opening 800, the irrigation tubing (not shown, see FIG. 4) is extended out of the distal end 818 of the maxillary lavage catheter 800.

As shown in FIG. 1, the proximal portion 106 of the maxillary lavage catheter 100 includes a proximal irrigation tube 120 with a proximal end 124 and a distal end 122. The proximal end 124 of the proximal irrigation tube 120 contains a luer connector 126 and the distal end connects to the proximal end 112 of the elongate shaft 108. The luer connector 126 connects the proximal end 124 of the proximal irrigation tube 120 with a source of irrigation for lavage of the maxillary sinus. A syringe (e.g., having a volume of about 10 cc to about 60 cc, for example) may be connected to luer connector 126. The syringe may be used to drive the irrigation fluid out of the atraumatic tip 118 by hand pressure by the operator on a hand pushable plunger of the syringe. Fluid pressures of about 4 to about 6 pounds per square inch (psi) are typically generated when using a 60 cc syringe, and pressures of about 15 to about 25 psi can be generated using a 10 cc syringe with flow rates of between about 50 ml/min and 250 ml/min, and often between about 75 ml/min and 125 ml/min. Alternatively, the luer connector 126 may be connected to a vacuum source to apply suction to the maxillary sinus. Further, a pulsation device may be included to achieve pulsatile delivery of the irrigation fluid. An in-line valve assembly may be included between the fluid source, in this case a syringe, and the catheter, in this case the luer connector 126. In a particular embodiment, to maximize irrigation efficiency, the valve assembly prevents flow when the applied force is low and allows fluid to pass one the pressure reaches a desired threshold.

Figure 9:
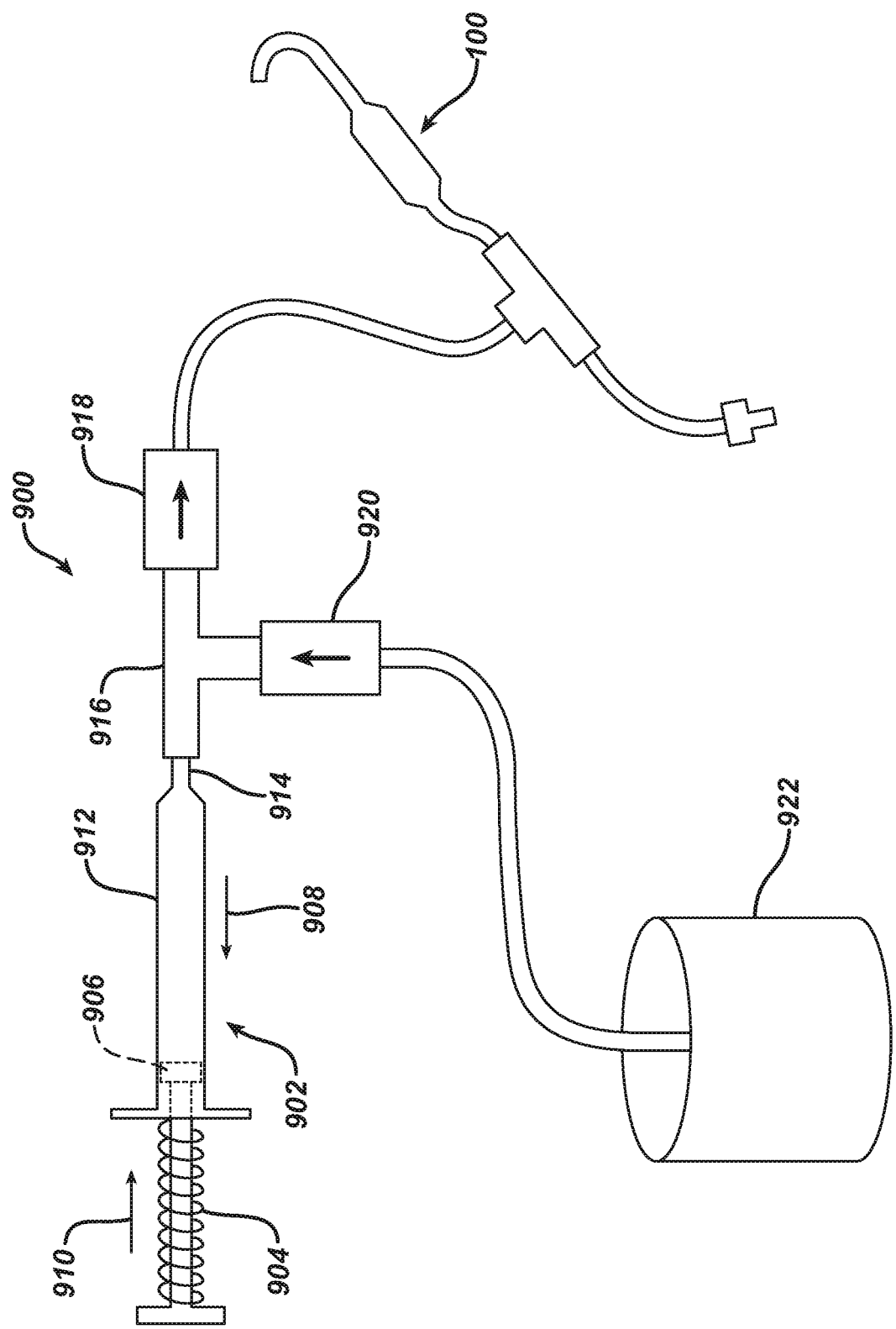
FIG. 9 is a schematic diagram of a continuous fluid injection system for use with the medical device according to the invention.

Further, a pump device 900 as shown in FIG. 9 may be included to allow the user to continuously inject irrigation fluid without having to disconnect and refill the syringe. The device 900 may be constructed of a syringe 902 with an integrated spring 904 that serves to force the plunger 906 back in the direction of arrow 908 after the user has squeezed the plunger 906 in the direction of arrow 910, toward the syringe body 912 and then released the pressure. The distal end 914 of the syringe 902 is attached to a connector 916. The connector 916 is also connected to a one-way exiting valve 918 and a one-way entering valve 920. Attached at the other side of the one-way exiting valve 918 is tubing leading to the maxillary lavage catheter 100 (shown in FIG. 1). Attached to the other side of the one-way entering valve 920 is a fluid reservoir 922, where the reservoir may be any type of fluid reservoir such as a fluid bath or a fluid bag. In this way, when the user pushers the plunger 906 in the direction of arrow 910, the fluid is force through the exiting one-way valve 918 to the maxillary lavage catheter 100. When the force on the plunger 906 is removed, the spring 904 forces the plunger back, drawing irrigation fluid from the fluid reservoir 922 through the entering one-way valve 920 and into the syringe body 912. Filling of the syringe may also be accomplished by the user pulling back on the plunger 906.

Direct visualization markers and/or radiographic markers may be disposed along the lavage catheter 100 distal portion 102. Generally, "direct visualization markers" refers to markers that may be viewed during use with the naked eye or by an endoscope. In one embodiment, flexible distal portion 102 may have a dark color, such as black, dark blue, dark grey or the like or may be transparent, and markers may have a light color, such as white, green, red or the like. In some embodiments, markers may have different colors and/or different widths to facilitate distinguishing the markers from one another during use. This contrast in colors may facilitate viewing the markers in a darkened operation room and/or when using an endoscope inside a patient in the presence of blood. Additionally one or more illumination fibers may be included in the lavage catheter 100 to confirm access of the maxillary sinus.

Lavage catheter 100 is configured to irrigate into and suction fluids out of the maxillary sinus. Lavage catheter 100 is sized appropriately to be delivered into adult as well as pediatric maxillary sinuses. Lavage catheter 100 can also be used to deliver diagnostic or therapeutic substances into the sinuses or other areas in the paranasal space. Examples of such diagnostic or therapeutic substances include, but are not limited to: contrast agents, pharmaceutically acceptable salt or dosage form of an antimicrobial agent (e.g., antibiotic, antiviral, anti-parasitic, antifungal, etc.), a corticosteroid or other anti-inflammatory (e.g., an NSAID), a decongestant (e.g., vasoconstrictor), a mucous thinning agent (e.g., an expectorant or mucolytic), an anesthetic agent with or without vasoconstrictor (e.g., Xylocaine with or without epinephrine, Tetracaine with or without epinephrine), an analgesic agent, an agent (anti-allergenic agent) that prevents of modifies an allergic response (e.g., an antihistamine, cytokine inhibitor, leucotriene inhibitor, IgE inhibitor, immunomodulator), an allergen or another substance that causes secretion of mucous by tissues, anti-proliferative agents, hemostatic agents to stop bleeding, cytotoxic agents e.g. alcohol, and biological agents such as protein molecules, stem cells, genes or gene therapy preparations.

In the method of the invention, the distal end of the lavage catheter 100 is inserted deep into the maxillary sinus. The actuator 142 is slid from a first position adjacent the proximal hub 132 to a second position adjacent the distal hub 136, there by advancing the atraumatic tip 118 of the distal irrigation tube 114 well into the maxillary sinus. Irrigation is performed as irrigation fluid is pushed through the opening 212 in the atraumatic tip 118 using a syringe or other fluid introduction device attached to the luer connector 126. Once lavage is complete, the actuator 142 is retracted back to its first position adjacent the proximal hub 132 and the lavage catheter 100 is removed from the patient's anatomy.

Figure 3:
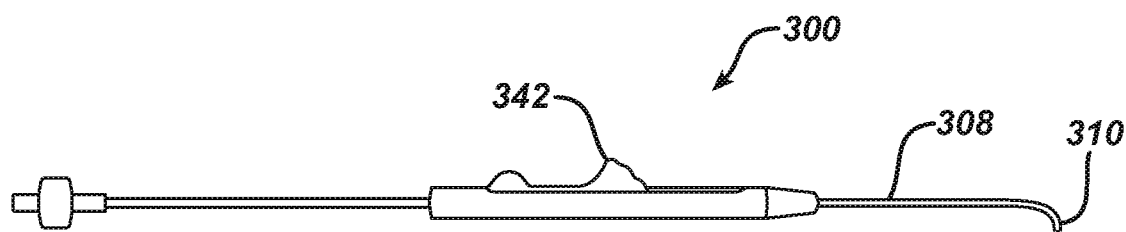
FIG. 3 is a side view of a further embodiment of the medical device according to the invention.
Figure 4:
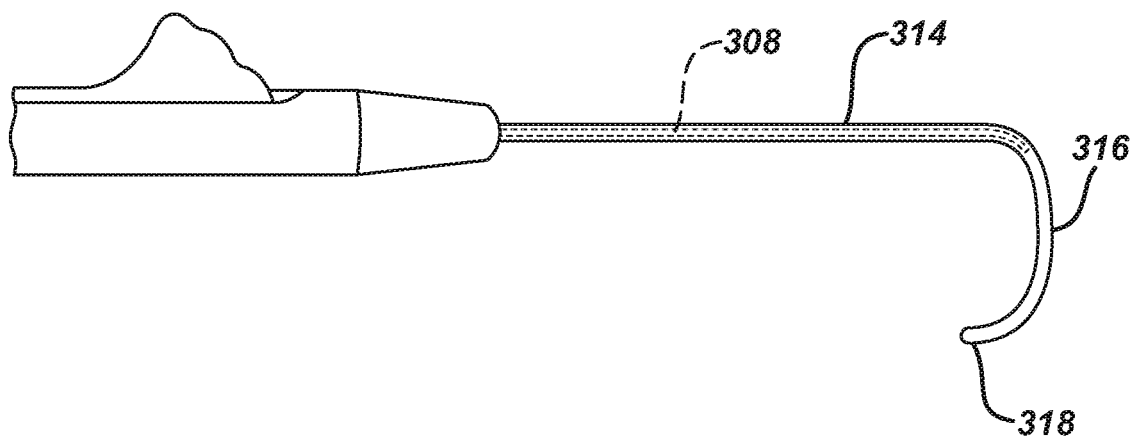
FIG. 4 is an enlarged view of the distal portion of the medical device of FIG. 3 in an extended configuration.

FIG. 3 is a side view of a maxillary lavage catheter 300 according to a further embodiment of the present invention. Similar to the lavage catheter 100 shown in FIGS. 1 and 2, the irrigation tube 314 coaxially surrounds the elongate shaft 308 (see FIG. 4). Once the distal end 310 of the catheter 300 is positioned behind the uncinate near the maxillary sinus, the distal end 316 of the irrigation tube 314 is advanced by sliding actuator 342 on handle 344 in the distal direction, thereby advancing irrigation tube 314 into the sinus where irrigation occurs. FIG. 3 shows the irrigation tube 314 prior to advancement, and FIG. 4 shows the irrigation tube 314 following advancement into the sinus. The irrigation tube 314 is sufficiently flexible to navigate through the infundibular space, enter the sinus atraumatically, and provide adequate irrigation when flushed with sterile water, saline, or other liquid from a standard syringe or fluid injection device. Irrigation takes place through the elongate shaft 308 and through irrigation holes at the distal end 316 of the irrigation tube 314. The narrow tip envelope and curve allow for easy access and positioning behind the uncinate. An atraumatic tip 318 prevents damage to surrounding tissue while locating the ostium. The small distal end 316 (approximately 1.5 mm to 2.5 mm in diameter) makes it easier to position the distal end 316 of the irrigation tube 314 behind the uncinate. This provides the irrigation tube 314 direction once it is actuated. The side irrigation holes of the distal end 316 and front blockage at the atraumatic tip 318 allow for spray in all directions to effectively clean the sinus. The atraumatic ball tip 318 minimizes the risk of tissue damage while accessing the sinus.

Figure 5:
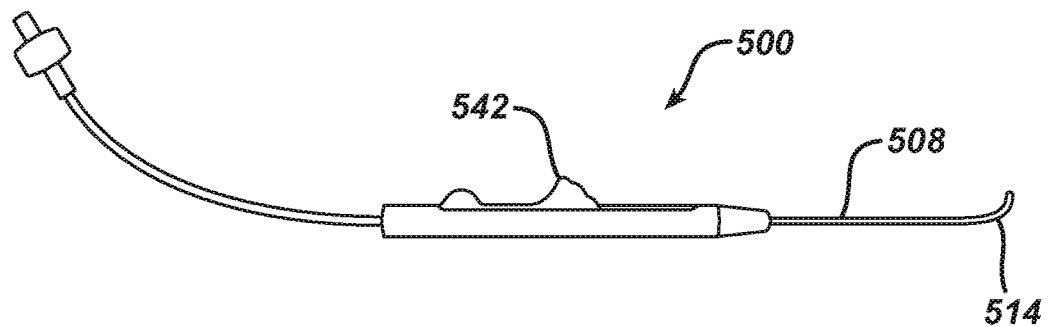
FIG. 5 is a side view of yet another embodiment of the medical device according to the invention.
Figure 6:
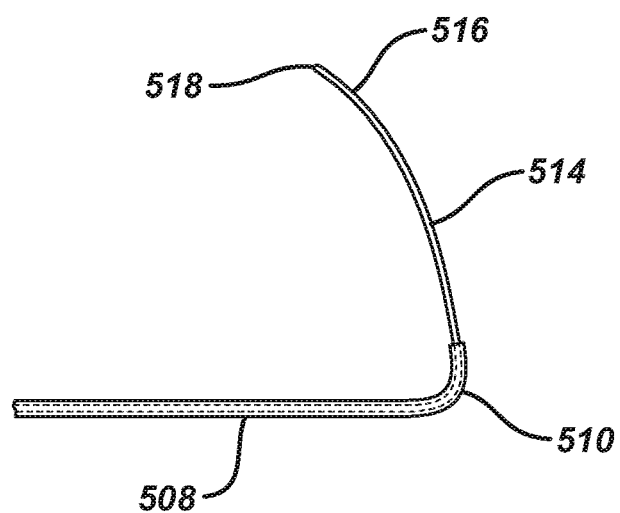
FIG. 6 is an enlarged view of the distal end of the medical device of FIG. 5 according to the invention.

FIG. 5 is a side view of a maxillary lavage catheter 500 according to a further embodiment of the present invention. In this embodiment, the irrigation tube 514 is coaxially surrounded by the elongate shaft 508 (see FIG. 6). Once the distal end 510 of the catheter 500 is positioned behind the uncinate near the maxillary sinus, the distal end 516 of the irrigation tube 514 is advanced by sliding actuator 542 in the distal direction, thereby advancing irrigation tube 514 into the sinus where irrigation occurs. FIG. 5 shows the irrigation tube 514 prior to advancement, and FIG. 6 shows the irrigation tube 514 following advancement into the sinus. The irrigation tube 514 is sufficiently flexible to navigate through the infundibular space, enter the sinus atraumatically, and provide adequate irrigation. Irrigation takes place through the elongate shaft 508 and through irrigation holes at the distal end 516 of the irrigation tube 514. The narrow tip envelope and curve allow for easy access and positioning behind the uncinate. An atraumatic tip 518 prevents damage to surrounding tissue while locating the ostium. The small distal end 516 (approximately 1.3 mm to 2.3 mm in diameter) makes it easier to position the distal end 516 of irrigation tube 514 behind the uncinate. This provides the irrigation tube 514 direction once it is actuated. The side irrigation holes and front blockage on the atraumatic tip 518 allow for spray in all directions to effectively clean the sinus. The atraumatic ball tip 518 minimizes the risk of tissue damage while accessing the sinus.

Figure 7:
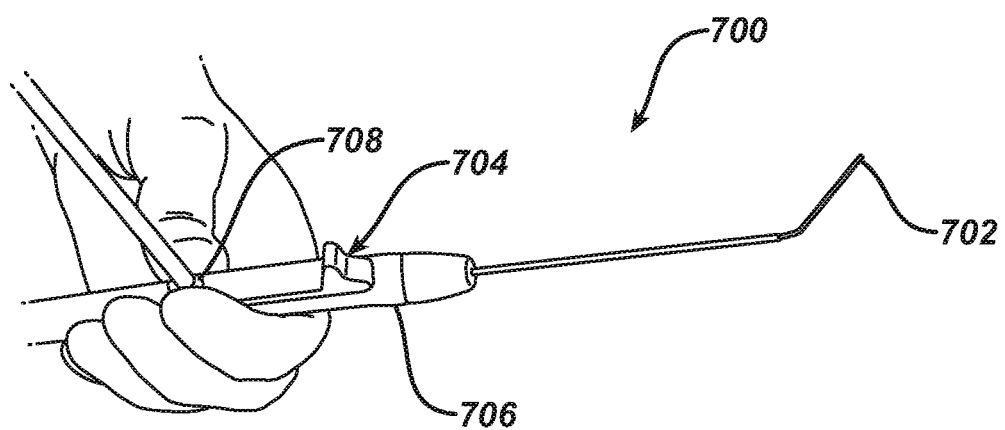
FIG. 7 is a top view of still another embodiment of the medical device according to the invention.

Delivery of the lavage catheter 100 of the current invention may be additionally or alternatively visualized by using an endoscope or by using fluoroscopy, electromagnetic or optical guidance, including 3-dimensional visualization such as CT or MRI visualization or other known visualization techniques. In one embodiment of the invention, one or more light fibers may be included in the lumen of the distal irrigation tube 114 such that advancement of the atraumatic tip 118 into the maxillary sinus can be observed as a result of the transillumination of the maxillary sinus. Alternatively, the distal irrigation tube 114 may comprise a dual lumen tube, one lumen for irrigation and one for containing the light fibers for transillumination of the maxillary sinus. In the embodiment of the invention shown in FIG. 7 a light fiber (or light fibers) can be integrated into the catheter 700 at the distal tip end 702 and the actuator 704 of the handle 706. The catheter 700 may be advanced into the sinus and positioned therein under endoscopic visualization. Once the catheter 700 is advanced into the sinus, the endoscope may be removed so that it can be used as a light source. The light end of the endoscope is placed at light access point 708 by placing it directly onto the actuator 704 as shown in FIG. 7. This configuration eliminates the need for an extra light source and requires no additional steps by the user. After confirmation, the endoscope can be placed back into the nasal cavity for further endoscopic visualization.

Figure 10A:
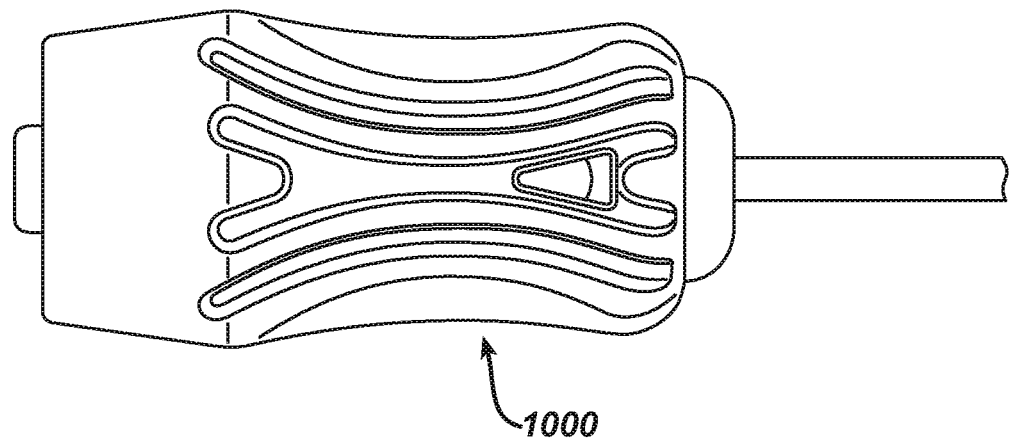
FIG. 10A is a light cable connector for use in connecting a light cable to the medical device according to the invention.
Figure 10B:
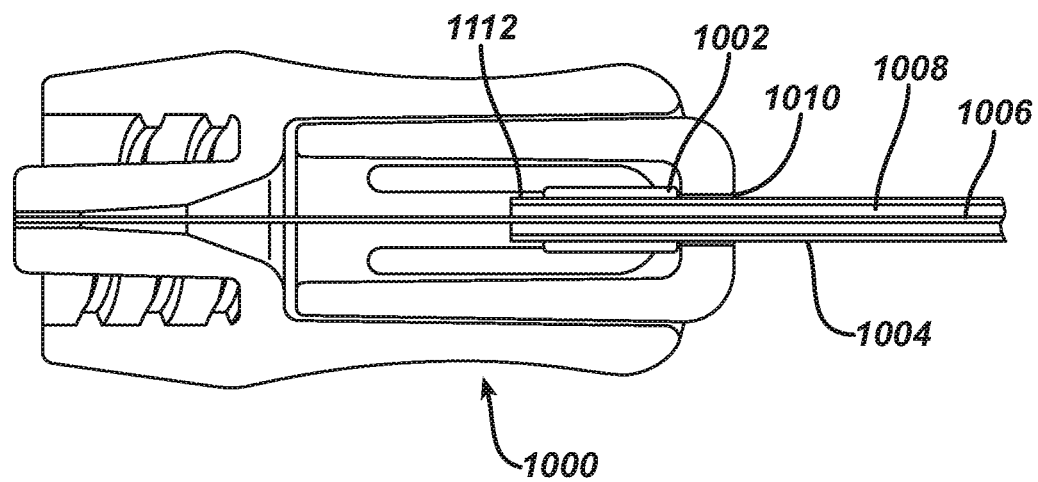
FIG. 10B is a side cut-away view of the light cable connector of FIG. 10A.

In an alternative embodiment, an extra light source could be provided to connect to the one or more light fibers. Connection of the one or more light fibers to the light source can be accomplished with a rotating light cable connector 1000 as shown in FIGS. 10A and 10B. Using this light cable connector 1000, the user can rotate the maxillary lavage catheter 100 while it is attached to a light source without the weight of the light cable (not shown) inhibiting rotation.

As shown in FIG. 10B, the connector 1000 contains a grommet 1002 that is attached to the proximal end 1112 of the tubing 1004. The light fiber 1006 (which may actually be one or more light fibers) is contained within the lumen 1008 of the tubing 1004. The grommet 1002 is designed to float freely inside the connector 1002, thereby allowing the tubing 1004 to spin freely when it is rotated. The grommet 1002 is larger than the distal hole 1010 of the connector 1000, such that the grommet 1002, and therefore the tubing 1004 is prevented from being pulled from the connector 1000 longitudinally.

The invention has been described with reference to certain examples or embodiments of the invention, but various additions, deletions, alterations and modifications may be made to those examples and embodiments without departing from the intended spirit and scope of the invention. For example, any element or attribute of one embodiment or example may be incorporated into or used with another embodiment or example, unless otherwise specified or if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A method comprising:
   (a) bending a malleable portion of a shaft assembly of an instrument from a first configuration to a second configuration, the second configuration defining a bend angle selected to promote access to a selected paranasal sinus ostium, the shaft assembly including:
      (i) an internal shaft member, the internal shaft member including the malleable portion, and
      (ii) an external shaft member positioned coaxially about the internal shaft member, the external shaft member being flexible, the external shaft member being operable to translate relative to the internal shaft member;
   (b) inserting a distal end of the shaft assembly through the selected paranasal sinus ostium and into a sinus cavity corresponding to the selected paranasal sinus ostium;
   (c) advancing an actuator of a handle assembly from a proximal position to a distal position, wherein the handle assembly extends proximally from the shaft assembly, the handle assembly including:
      (i) a proximal end,
      (ii) a distal end, and
      (iii) the actuator positioned between the proximal end of the handle assembly and the distal end of the handle assembly, the actuator being slidable between a proximal position and a distal position, the actuator being configured to remain positioned between the proximal end of the handle assembly and the distal end of the handle assembly when the actuator is in the proximal position, the actuator being further configured to remain positioned between the proximal end of the handle assembly and the distal end of the handle assembly when the actuator is in the distal position,
   (d) communicating irrigation fluid through one or more lateral openings formed in the shaft assembly to thereby irrigate the sinus cavity; and
   (e) applying suction through the shaft assembly.

2. The method of claim 1, the external shaft member advancing distally relative to the internal shaft member in response to the actuator being advanced from the proximal position to the distal position.

3. The method of claim 2, the external shaft member being advanced distally to a point where a distal end of the internal shaft member is proximal to a distal end of the external shaft member in response to the actuator being advanced from the proximal position to the distal position.

4. The method of claim 2, wherein advancing the actuator is performed before applying suction.

5. The method of claim 2, wherein advancing the actuator is performed before communicating irrigation fluid.

6. The method of claim 2, the external shaft member conforming to the bend angle defined by the internal shaft member as the external shaft member is advanced distally.

7. The method of claim 1, the shaft assembly further including a ball tip, wherein inserting a distal end of the shaft assembly through the selected paranasal sinus ostium comprises passing the ball tip through the selected paranasal sinus ostium.

8. The method of claim 1, wherein the selected paranasal sinus ostium comprises a maxillary sinus ostium.

9. The method of claim 8, wherein the bend angle is between 90 degrees and 140 degrees.

10. The method of claim 9, wherein the bend angle is between 100 degrees and 130 degrees.

11. The method of claim 1, wherein the internal shaft member comprises stainless steel.

12. The method of claim 1, wherein the external shaft member comprises a polymeric material.

13. The method of claim 1, wherein the external shaft member comprises a flexible material selected from the group consisting of nylon, polyethylene, polyether ether ketone or polyether block amides.

14. The method of claim 1, wherein the irrigation fluid is communicated through the one or more lateral openings formed in the external shaft member.

15. The method of claim 14, wherein the irrigation fluid and the suction are both communicated through the external shaft member.

16. The method of claim 1, wherein the suction is applied through the external shaft member.

17. The method of claim 1, wherein communicating irrigation fluid comprises actuating a syringe.

18. A method comprising:
(a) bending a malleable portion of a shaft assembly of an instrument from a first configuration to a second configuration, the second configuration defining a bend angle between 90 degrees and 140 degrees, the shaft assembly including:
  (i) an internal shaft member, the internal shaft member including the malleable portion, and
  (ii) an external shaft member positioned coaxially about the internal shaft member, the external shaft member being flexible, the external shaft member being operable to translate relative to the internal shaft member;
(b) grasping a handle assembly of the instrument, the handle assembly including:
  (i) a proximal end,
  (ii) a distal end, and
  (iii) an actuator positioned between the proximal end of the handle assembly and the distal end of the handle assembly, the actuator being slidable between a proximal position and a distal position, the actuator being configured to remain positioned between the proximal end of the handle assembly and the distal end of the handle assembly when the actuator is in the proximal position, the actuator being further configured to remain positioned between the proximal end of the handle assembly and the distal end of the handle assembly when the actuator is in the distal position,
the shaft assembly extending distally relative to the distal end of the handle assembly
(c) while grasping the handle assembly, inserting a distal end of the shaft assembly through a maxillary sinus ostium; and
(d) communicating irrigation fluid through one or more lateral openings formed in the shaft assembly to thereby irrigate the maxillary sinus cavity.

19. A method comprising:
(a) bending a malleable portion of a shaft assembly of an instrument from a first configuration to a second configuration, the second configuration defining a bend angle between 90 degrees and 140 degrees, the shaft assembly including:
  (i) a first shaft member, and
  (ii) a second shaft member positioned coaxially with the first shaft member;
(b) grasping a handle assembly of the instrument, the handle assembly including:
  (i) a proximal end,
  (ii) a distal end, and
  (iii) an actuator positioned between the proximal end of the handle assembly and the distal end of the handle assembly, the actuator being slidable between a proximal position and a distal position, the actuator being configured to remain positioned between the proximal end of the handle assembly and the distal end of the handle assembly when the actuator is in the proximal position, the actuator being further configured to remain positioned between the proximal end of the handle assembly and the distal end of the handle assembly when the actuator is in the distal position,
the shaft assembly extending distally relative to the distal end of the handle assembly
(c) while grasping the handle assembly, inserting a distal end of the shaft assembly through a maxillary sinus ostium;
(d) advancing the actuator distally from the proximal position to the distal position, thereby advancing the second shaft member distally relative to the first shaft member; and
(e) applying suction through the distally advanced second shaft member.

20. The method of claim 1, further comprising grasping the handle assembly of the instrument with a hand and advancing the actuator with a finger or thumb of the hand.

* * * * *